United States Patent [19]

Parins

[11] Patent Number: 5,083,565
[45] Date of Patent: Jan. 28, 1992

[54] ELECTROSURGICAL INSTRUMENT FOR ABLATING ENDOCARDIAL TISSUE

[75] Inventor: David J. Parins, Columbia Heights, Minn.

[73] Assignee: Everest Medical Corporation, Minneapolis, Minn.

[21] Appl. No.: 562,882

[22] Filed: Aug. 3, 1990

[51] Int. Cl.⁵ ..................... A61B 5/0402; A61B 17/36
[52] U.S. Cl. ..................................... 128/642; 128/786; 606/41; 606/48
[58] Field of Search .................. 128/642, 786; 606/33, 606/41, 45, 46, 48, 49, 50

[56] References Cited

U.S. PATENT DOCUMENTS

| | | |
|---|---|---|
| 4,641,649 | 2/1987 | Walinsky et al. |
| 4,660,571 | 4/1987 | Hess et al. ........................ 128/642 X |
| 4,785,815 | 11/1988 | Cohen ................................. 128/642 |

FOREIGN PATENT DOCUMENTS

| | | | |
|---|---|---|---|
| 2560052 | 8/1985 | France | 128/786 |
| 1140792 | 2/1985 | U.S.S.R. | 128/786 |

Primary Examiner—Lee S. Cohen
Attorney, Agent, or Firm—Haugen and Nikolai

[57] ABSTRACT

An endocardial electrosurgical catheter for locating and subsequently ablating ectopic foci in cardiac tissue comprises an elongated flexible tubular catheter sized to permit its being routed through the vascular system and into a cardiac chamber of the heart. The elongated catheter includes at least one pair of spaced bipolar sensing electrodes near its distal end whereby depolarization signals develop within the heart can be picked up and transmitted over electrical conductors passing through the lumen of the tubular catheter body to be applied to a EKG monitor. Also extending through the lumen of the tubular catheter body are a pair of conductors whose distal ends may selectively be made to project from or be retracted into the body of the catheter. A RF voltage from an electrosurgical generator may be coupled to the proximal ends of the wires and when the uninsulated distal ends thereof are extended so as to pierce into the myocardium, the RF voltage may be used to destroy the cells comprising an ectopic focus.

2 Claims, 1 Drawing Sheet

U.S. Patent  Jan. 28, 1992  5,083,565
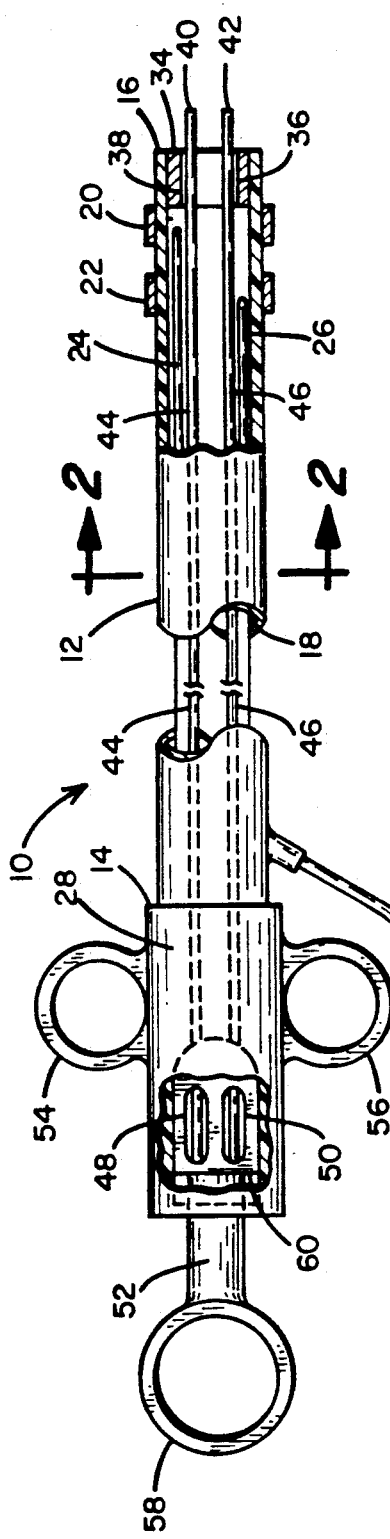
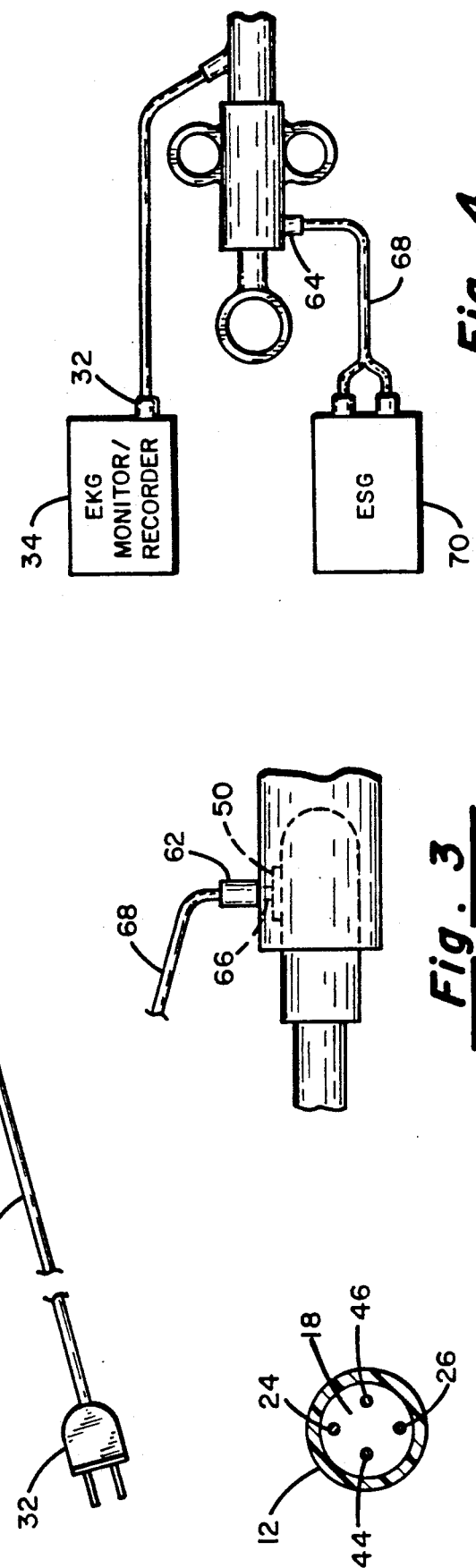

ELECTROSURGICAL INSTRUMENT FOR ABLATING ENDOCARDIAL TISSUE

BACKGROUND OF THE INVENTION

I. Field of the Invention

This invention relates generally to electrosurgical apparatus, and more particularly to a catheterlike device capable of being routed through the vascular system and having a first set of sensing electrodes for mapping ectopic foci within the myocardium and a second set of bipolar electrodes which may be used to ablate myocardial tissue to remove such ectopic foci.

II. Discussion of the Prior Art

Natural cardiac pacing, under normal circumstances, begins with depolarization of sinoatrial (S-A) node which spreads an electrical impulse from its location in the right atrium across to the left atrium and downward towards the ventricles. The depolarization wave reaches the transition zone between the atrium and the ventricles where the atrio-ventricular (A-V) node or junction is located. When this node fires, the impulse is passed down the Bundle of His, between the right and left ventricles, and into the right and left bundle branches, each branch supplying one ventricle. These bundle branches then divide into finer paths of conducting tissue which spread from the inner to the outer surfaces of the heart and which are referred to as the Purkinje fibers. These fibers feed the depolarization impulse into all portions of the ventricular myocardium. Certain tachyrhythmias can be traced to the existence of ectopic foci. For example, atrial tachycardia may result when an alternative pacemaker focus in the atrium, i.e., a focus other than the S-A node, fires at a higher rate than the S-A node. If the ectopic foci is in the ventricle, it may lead to ventricular tachycardia and more seriously to ventricular fibrillation.

A number of drugs are available for treating ventricular tachycardia and other ventricular arrhythmias, such as lidocaine, quinidine and procaineamide. Beta-blocking drugs, such as propranolol, may also be used where there is an excess of either sympathetic nervous activity or adrenal secretion.

Where drug therapy is ineffective to arrest episodes of lifethreatening tachyrhythmias, surgical procedures have been used to remove ectopic foci appearing in either or both of the atrium and ventricles. Generally, the surgical procedures have involved open heart surgery wherein a thoracotomy is required to gain access to the heart. An incision is made through the pericardium and the heart muscle is mapped to locate the sites of the ectopic foci. The involved myocardial tissue is then surgically removed, thereby replacing the excitable tissue with scar tissue. Open heart surgery is a relatively traumatic procedure requiring a prolonged period of hospitalization and a long period of recuperation.

Various cardiac procedures have been devised for treating a number of cardiac abnormalities in which a catheter is used to correct the defect. For example, stenotic lesions, accompanying coronary artery disease, are now routinely treated using balloon angioplasty. In this procedure, an elongated, flexible, plastic tube having an inflatable balloon at its distal end may be routed through the vascular system from a location on the patient's leg and when the balloon is appropriately positioned across the site of the lesion, an inflation fluid is injected through the lumen of the catheter to expand the balloon and thereby open up the clogged or partially clogged coronary blood vessel. In a valvuloplasty procedure, a catheter is again routed through the vascular system with the balloon being positioned in the valve to be treated. Upon inflation of the balloon, the calcified deposits binding the valve leaflets together is ruptured, restoring the flexibility to the valve tissues.

SUMMARY OF THE INVENTION

In accordance with the present invention, an elongated flexible tubular catheter is provided with that catheter having a proximal end, a distal end and a lumen extending therebetween. The outside diameter of the tubular catheter allows it to be routed through the vascular system and into the heart chamber to be treated. Disposed on the outside surface of the tubular catheter near the distal end thereof are first and second conductive ring electrodes which are spaced apart a predetermined distance and which are connected by electrical conductors extending through the lumen of the catheter to its proximal end. These conductors may be coupled to a suitable EKG system for measuring and displaying cardiac depolarization potentials sensed within the involved cardiac chamber. In this fashion, the location of ectopic foci can be mapped.

The catheter further includes a second set of bipolar electrosurgical electrodes which can be extended out from or retracted into the distal end of the tubular catheter by appropriately manipulating a slide mechanism at the proximal end of the tubular catheter. Electrical conductors extending the length of the catheter are coupled to the bipolar electrosurgical electrodes and means are provided at the proximal end of the instrument to couple those conductors to appropriate terminals of an electrosurgical generator. When the mapping procedure locates an ectopic focus to be removed, the bipolar electrosurgical electrodes are made to project out from the catheter's distal end and penetrate into the myocardial tissue at the site of the focus to be treated. Now, by applying an appropriate RF voltage to the electrodes, a small segment of tissue determined by the spacing between the two electrodes can be ablated to thereby prevent that tissue from spontaneously depolarizing and contributing to the tachyrhythmia. Because the procedure can be carried intravascularly, it is substantially less traumatic than the prior art open heart surgical approach at surgical ablation of myocardial tissue. Moreover, the amount of power to effect ablation is reduced and the resulting damage to neighboring tissue is minimized.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

FIG. 1 is a top elevational view of the electrosurgical instrument of the present invention partially cross-sectioned to expose internal working parts thereof;

FIG. 2 is a cross-sectional view taken along the line 2-2 in FIG. 1;

FIG. 3 is a partial side elevational view of the proximal end portion of the device of FIG. 1; and FIG. 4 illustrates the manner in which the instrument of the present invention ma be electrically coupled to both an EKG monitor and an electrosurgical generator.

DESCRIPTION OF THE PREFERRED EMBODIMENT

Referring first to FIG. 1, there is indicated generally by numeral 10 the electrosurgical instrument of the present invention useful in ablating myocardial tissue. It is seen to comprise an elongated, flexible plastic tubular member 12 having a proximal end 14 and a distal end 16 with at least one lumen 18 extending between the proximal and distal ends thereof. The outside diameter of the instrument may typically be about 7-8 French, allowing it to readily pass through the lumen of an introducer (not shown) in the same fashion that angiographic and angioplasty catheters are now routed through the vascular system such that the distal end portion thereof may be positioned in a selected cardiac chamber. A variety of plastic materials are available including polyethylene, polyurethane, nylon and polyester, with the polymers being blended to afford a desired degree of flexibility combined with pushability and torqueability to facilitate placement.

Located just proximal of the distal end 16 of the tube 12 and mounted on its exterior surface are first and second conductive rings 20 and 22 which form a bipolar pair of sense electrodes. The electrodes 20 and 22 are coupled by wires 24 and 26 which run the full length of the catheter body and exit a proximal hub 28, via cord 30, and terminate in a plug 32. As shown in FIG. 4, the plug 32 is adapted to couple the sense electrodes 20 and 22 to terminals of a EKG monitor/recorder 34 of known design. While only two rings are shown, it is to be understood that additional ring electrodes may be included on the surface of the tube 12.

Disposed in the lumen 18 of the tube 12 proximate its distal end 16 is a spacer 34 having longitudinal bores 36 and 38 formed therethrough. As can be seen in FIG. 1, extending outwardly beyond the distal end 16 of the instrument are the distal ends 40 and 42 of electrical conductors 44 and 46 which extend the entire length of the tubular catheter body 12 and into the hub 28 where they join to conductive connectors 48 and 50 affixed to a reciprocally movable plunger member 52 which is fitted into a bore formed in the hub 28. The conductors 44 and 46 are covered with a thermoplastic insulating material except at the tips 40 and 42 thereof. The hub 28 is preferably fabricated in a molding operation from any one of several medical grade plastics. Projecting laterally outward from the opposed sides of the hub 28 are finger loops 54 and 56 and affixed to the proximal end of the plunger member 52 is a ring 58 having an opening therein for receiving the user's thumb. Thus, by flexing the thumb relative to the forefinger and index finger cradled in the loops 54 and 56, the distal ends 40 and 42 of the conductors 44 and 46 can be retracted out into the bores 36 and 38 in the spacer 34 or, alternatively, can be extended out as shown in FIG. 1. By providing a shoulder on the plunger 52 as at 60, a stop is provided to prevent the distal ends 40 and 42 of the conductors 44 and 46 from retracting to the point where they no longer extend into the bores 36 and 38. The plunger may also utilize an adjustable forward stop to preset the extent of projection of the tips 40 and 42 and, therefore, their extent of penetration into the tissue.

Referring to the partial view of FIG. 3, it can be seen that plug 62 fits into jacks 66 in the hub, and when so inserted, cooperate with the connectors 48 and 50 to establish a sliding electrical connection between the wires 44 and 46 and conductors 68 leading to RF power output terminals of an electrosurgical generator (ESG) 70.

In use, the catheter of the present invention may be routed through the vascular system and into the right or left atrium or into the right or left ventricle. By manipulating the catheter and by using fluoroscopic techniques, the location where ectopic beats originate can be located using the EKG monitor/recorder 34 to pick up, display and record the depolarization signals being sensed by the ring electrodes 20 and 22 on the distal end of the catheter tube 12. Once the endocardial surfaces have been mapped to locate ectopic foci, the next step in the procedure is to abut the distal end 16 of the catheter against the tissue at the site of an ectopic focus and then, by compressing the plunger 52 into the hub member 28, the distal ends 40 and 42 of the conductors 44 and 46 are pushed out from the distal end of the catheter and pierce into the myocardial tissue to a predetermined depth. Now, by appropriately depressing a foot pedal control (not shown) associated with the electrosurgical generator 70, a RF current is made to flow through the tissue located between the non-insulated projecting tips of the conductors 44 and 46 to destroy the excitable tissue in question and to thereby eliminate that site as an ectopic focus responsible for the episodes of tachyrhythmia.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. An endocardial electrosurgical catheter for locating and subsequently ablating an ectopic foci in a patient's heart, comprising:
   (a) an elongated, flexible, plastic tubular catheter body having a proximal end, a distal end, an outer surface and at least one lumen extending from said proximal end to said distal end;
   (b) bipolar surface electrodes affixed to said outer surface of said catheter body at longitudinally spaced apart locations approximate said distal end of said catheter body;
   (c) first and second elongated, conductive wires extending through said lumen and electrically joined, individually, to said first and second bipolar surface electrodes at one end;
   (d) means connected to the other end of said first and second conductive wires for coupling said first and second conductive wires to EKG monitoring/recorder means;
   (e) third and fourth elongated conductive wires, each having a proximal end and a distal end and extending through said lumen, said third and fourth conductive wires being insulated from one another and longitudinally movable within said lumen;
   (f) insulative spacer means disposed in said lumen at said distal end of said catheter body for maintaining said distal ends of said third and fourth wires laterally spaced relative to one another, said distal ends of said third and fourth wires being free of insulation; and (g) means affixed to said proximal end of said catheter body and to said third and fourth wires for longitudinally moving said third and fourth wires from a retracted position wherein said distal ends of said third and fourth wires are unexposed relative to said distal end of said tubular catheter body and an exposed position wherein said distal ends of said third and fourth wires extend beyond of said distal end of said tubular catheter body.

2. The electrosurgical catheter as in claim 1 wherein said means affixed to said proximal end of said catheter body comprises:

(a) a hub member affixed to said proximal end of said catheter body and including a longitudinal bore;

(b) a manually operable plunger fitted into said bore in said hub member and reciprocally movable therein, said plunger including first and second electrical contact pads to which said proximal end of said third and fourth elongated conductive wires attach; and (c) means cooperating with said conductive pads for applying a RF voltage between said third and fourth conductive wires.

* * * * *